United States Patent [19]

Machida et al.

[11] Patent Number: 4,794,930
[45] Date of Patent: Jan. 3, 1989

[54] ATTACHMENT FOR DIAGNOSTIC ULTRASOUND PROBE

[75] Inventors: Kaoru Machida, Ootawara; Akifumi Suzuki; Yushichi Kikuchi, both of Nishinasunomachi; Masayuki Takano, Ootawara, all of Japan

[73] Assignee: Kabushiki Kaisha Toshiba, Kawasaki, Japan

[21] Appl. No.: 103,813

[22] Filed: Oct. 2, 1987

[30] Foreign Application Priority Data

Oct. 3, 1986 [JP] Japan .............................. 61-235771
Nov. 6, 1986 [JP] Japan .............................. 61-264775

[51] Int. Cl.$^4$ .............................................. A61B 10/00
[52] U.S. Cl. .................................. 128/662.03; 73/644
[58] Field of Search ................. 73/624, 625, 627, 628, 73/632, 633, 644; 128/660

[56] References Cited

U.S. PATENT DOCUMENTS

| | | | |
|---|---|---|---|
| Re. 30,926 | 5/1982 | Ross et al. .............................. | 73/644 |
| 2,984,756 | 5/1961 | Bradfield .............................. | 73/644 |
| 4,474,184 | 10/1984 | Harui .................................. | 73/644 |

*Primary Examiner*—Francis J. Jaworski
*Assistant Examiner*—George Manuel
*Attorney, Agent, or Firm*—Finnegan, Henderson, Farabow, Garrett, & Dunner

[57] ABSTRACT

An attachment to a diagnostic ultrasound probe having a beam radiating surface from which ultrasound beam is radiated in a first plane toward a skin surface of an organic body through the attachment which comprises a reservoir section containing acoustic medium. The reservoir section includes an auxiliary membrane, a contact membrane, and a first plane. The auxiliary membrane has an outer surface in contact with the beam radiating surface and is capable of transmitting an ultrasound beam. The contact membrane is arranged to face the auxiliary membrane, has an outer surface in contact with the skin surface of an organic body, and an inner surface, and is capable of transmitting an ultrasound beam. The first wall connects the auxiliary membrane with the contact membrane and has the inner surface crossing the first plane. When an ultrasound beam is radiated from the beam radiating surface and transmitted to the contact membrane, the ultrasound beam is split into a component transmitted through the contact membrane and transferred to the skin surface in the first plane, and the remaining component reflected by the inner surface of the contact membrane. When the remaining component of ultrasound beam is transferred to the first wall in the first plane, a major part of ultrasound beam reflected by the inner surface of the first wall is prevented from being returned to the contact membrane to be reflected by the inner surface thereof, and from being returned to the beam radiating surface.

8 Claims, 9 Drawing Sheets

ATTACHMENT FOR DIAGNOSTIC ULTRASOUND PROBE

BACKGROUND OF THE INVENTION

This invention relates to an attachment for diagnostic ultrasound probe and, more particularly, to an attachment which is to be mounted in an ultrasound probe when examining an organ present in the neighborhood of the surface of the body.

The ultrasound probe has a transducer array having a plurality of transducer elements aligned in one direction. An ultrasound beam is emitted from the transducer elements to the body along a scanning plane. Ultrasound beam reflected by the interior of the body is received by the transducer elements. The body thus is scanned by the ultrasound beam along the scanning plane. The received ultrasound beam is converted into an electric signal so that a tomographic image of the body is displayed on a cathode-ray tube.

When an organ present in the neighborhood of the surface of the body is examined, an attachment accommodating an acoustic medium is mounted in an ultrasound probe. FIG. 1 shows this attachment. Attachment 2 comprises box-like reservoir section 3 accommodating an acoustic medium and mounting section 4 for mounting reservoir section 3 in ultrasonic probe 1. FIG. 2 schematically shows reservoir section 3. Reservoir section 3 includes auxiliary membrane 5 which is held in contact with ultrasound probe 1 and can transmit ultrasound beam, and contact membrane 6 which is disposed such that it faces auxiliary membrane 5, held in contact with the body and can transmit ultrasound beam. Reservoir section has a pair of side walls 8 which extend at right angles to scanning plane 7 and have one end connected to contact member 6, and a pair of top walls 9 which extend at right angles to scanning plane 7 and substantially parallel to contact membrane 6 and have one end connected to auxiliary membrane 5.

A major part of the ultrasound beam emitted from ultrasound probe 1 is transmitted through auxiliary membrane 5 and contact membrane 6, to be transferred to the body. However, the remaining part of the ultrasound beam is reflected by the inner surface of contact membrane 6, to be transferred to side walls 8 for multiplex reflection. More specifically, as shown by arrows in FIGS. 1 and 2, the ultrasound beam is transferred along first path 11 in scanning plane 7. Side walls 8 extend perpendicular to scanning plane 7. A part of the ultrasound beam reflected by the inner surface of side walls 8 is returned along first path 11 in scanning plane 7 to contact membrane 7, to be reflected by the inner surface thereof and returned to ultrasound probe 1. The returned ultrasound beam contains data concerning side walls 8. Thus, an image of side walls 8 is displayed on cathode-ray tube 28 as artifact, as shown by broken lines in FIG. 14. For this reason, it is liable that accurate diagnosis is prevented.

FIGS. 3 and 4 show an attachment, in which the distance between the lower ends of pair side walls 8 is greater than the distance between the upper ends of the side walls. Again in this attachment, side walls 8 extend at right angles to scanning plane 7, so that a part of the ultrasound beam reflected by the inner surfaces of side walls 8 is returned along first path 11 to contact membrane 8 and thence returned to ultrasound probe 1. For this reason, it is liable that an image of side walls 8 is displayed on cathode-ray tube.

Further, a part of the ultrasound beam emitted from ultrasound probe 1 and reflected by the inner surface of contact membrane 6 is liable to be transferred to top walls 9 for multiplex reflection. More specifically, as shown by arrows in FIGS. 1 to 4, the ultrasound beam reflected by the inner surface of contact membrane 6 is transferred along second path 12 in scanning plane 7. Top walls 9 extend substantially parallel to contact membrane 6. A part of the ultrasound beam reflected by the inner surface of top walls 9 is returned along second path 12 in scanning plane 7 to contact membrane 6, to be reflected by the inner surface thereof and returned to ultrasound probe 1. For this reason, like the case described above, the returned ultrasound beam has data concerning top walls 9. An image of top walls 9 thus is displayed as artifact on the cathode-ray tube.

Further, as is described above, reservoir section 3 accommodates an acoustic medium. This acoustic medium is, for example, water or colloidal material. When the acoustic medium is poured into reservoir section 3, air is liable to enter reservoir section 3. There is a possibility that the organic body is scanned by the ultrasound probe while the probe is disposed perpendicular to the body. At this time, auxiliary membrane 5 extends horizontally. For this reason, it is liable that air, i.e., air bubbles, is retained on the lower surface of auxiliary membrane 5, as shown in FIGS. 1 and 3. In this case, the ultrasound beam is blocked by air bubbles, resulting in deterioration of the quality of the tomographic image displayed on the cathode-ray tube. In such a case, air is expelled as much as possible by means of frequently replenishing reservoir section 3 with the acoustic medium. Even with this means, however, it is difficult to perfectly expel air from reservoir section 3.

SUMMARY OF THE INVENTION

An object of the invention is to provide an attachment for diagnostic ultrasound probe, which can reduce multiplex reflection of ultrasound beam in the reservoir section so that an image of reservoir section hardly is displayed on the cathode-ray tube and hardly prevents accurate diagnosis.

A further object of the invention is to provide an attachment for a diagnostic ultrasound probe, which is free from the deterioration of the quality of a tomographic image by air bubbles in the reservoir section.

According to the present invention, there is provided an attachment capable of being attached to a diagnostic ultrasound probe having a beam radiating surface from which ultrasound beam is radiated in a first plane toward a skin surface of an organic body through the attachment, which attachment comprises:

a reservoir section containing acoustic medium,
the reservoir section including:
an auxiliary membrane having an outer surface in contact with the beam radiating surface and capable of transmitting an ultrasound beam;
a contact membrane arranged to face the auxiliary membrane, having an outer surface in contact with the skin surface of an organic body and an inner surface and capable of transmitting an ultrasound beam, an ultrasound beam being radiated from the beam radiating surface, transmitted through the acoustic medium and transferred to the contact membrane, to be split into a component transmitted through the contact membrane and transferred to the skin surface in the first plane, and the remaining component reflected by the inner surface of the contact membrane; and a first wall connecting the auxiliary membrane with contact membrane and having the inner surface crossing the first plane, wherein when the component of the ultrasound beam reflected by the inner surface of the contact membrane is transferred to the first wall in the first plane, a major part of ultrasound beam reflected by the inner surface of the first wall is prevented from being returned to the contact membrane to be reflected by the inner surface thereof, and from being returned to the beam radiating surface.

For this reason, a major part of the ultrasound beam reflected by the first wall is not received by the ultrasound probe. Thus, data concerning the first wall is not input to the ultrasound probe, and an image of the first wall is hardly shown on the cathode-ray tube. For this reason, there is no possibility that accurate diagnosis is prevented by an image of the first wall.

More specifically, the first wall includes:

a second wall (a side wall) having one end and the other end and an inner surface crossing the first plane, the afore-said one end being connected to the contact membrane, and a third wall (a top wall) having one end and the other end and an inner surface crossing the first plane, the afore-said one end being connected to the auxiliary membrane, the afore-said other end being connected to the other end of the second wall (side wall).

The inner surface of the second wall (side wall) is inclined with respect to the first plane. Thus, when the component of the ultrasound beam reflected by the inner surface of the contact membrane is transferred to the second wall (the side wall) in the first plane, a major part of ultrasound beam reflected by the inner surface of the second wall (side wall) is transferred to any other than the first place. The ultrasound probe receives only the ultrasound beam in the scanning plane, so that the major part of ultrasound beam reflected by the inner surface of the side wall is not received by the ultrasound probe. This means that a component of ultrasound beam that is reflected by the inner surface of the side wall and returned to the contact membrane and thence to the ultrasound probe is extremely reduced. There is thus hardly a possibility that an image of the side wall is shown on the cathode-ray tube.

Further, the inner surface of the third wall (top wall) is inclined with respect to the contact membrane such that the distance between the other end of the third wall and contact membrane is greater than the distance between one end of the third wall and contact membrane. For this reason, when the component of the ultrasound beam reflected by the inner surface of the contact membrane is transferred to the third wall (top wall) in the first plane, a major part of ultrasound beam reflected by the inner surface of the third wall (top wall) is transferred in a direction (sidewise) away from the auxiliary membrane. For this reason, like the case noted above, a component of ultrasound beam that is reflected by the inner surface of the top wall and returned to the contact membrane and thence to the ultrasound probe is extremely reduced. For this reason, there is hardly a possibility that an image of the top wall is shown on the cathode-ray tube.

Further, the reservoir section includes air storage means, which is disposed adjacent to the auxiliary membrane and collects and stores air in the reservoir. There is a possibility that the organic body is scanned by the ultrasound probe while the probe is disposed perpendicular to the body. In this case, air bubbles in the reservoir section are displaced upwards, to be collected in the air storage means. For this reason, unlike the prior art there is no possibility that the ultrasound beam received by the probe is blocked by air bubbles. There is thus no possibility of deterioration of the quality of a tomographic image by air bubbles.

BRIEF DESCRIPTION OF THE DRAWINGS

FIGS. 10 and 11 illustrate a first modification of the invention, in which FIG. 10 is a sectional view of the attachment taken along plane parallel to the scanning plane, and FIG. 11 is a schematic perspective view showing a reservoir section of the attachment of FIG. 10;

DETAILED DESCRIPTION OF THE PREFERRED EMBODIMENTS

FIGS. 5 to 9 illustrate attachment 30 for diagnostic ultrasound probe 20, according to the invention. For the sake of the simplicity, it is assumed that attachment 30 is disposed on a horizontal plane and is mounted perpendicularly with respect to ultrasound probe 20.

Figure 1:
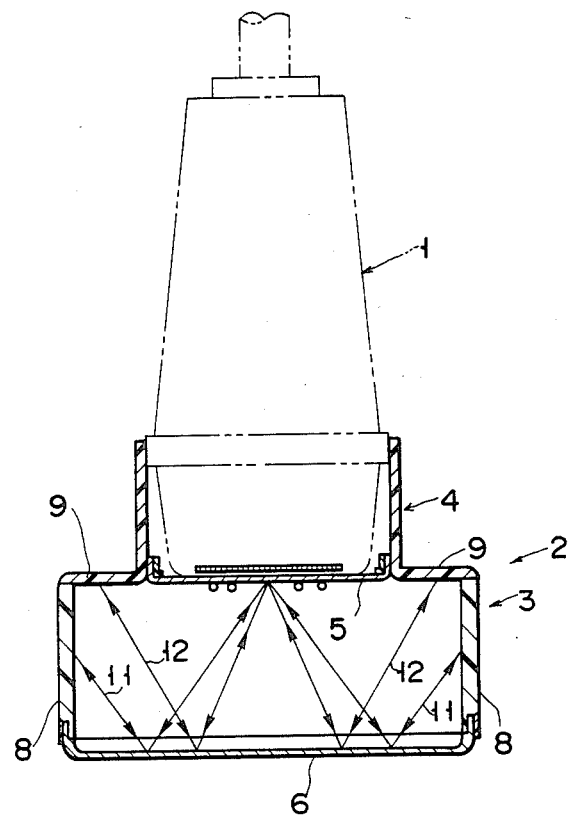
FIG. 1 is a sectional view showing a prior art attachment for a diagnostic ultrasound probe.
Figure 2:
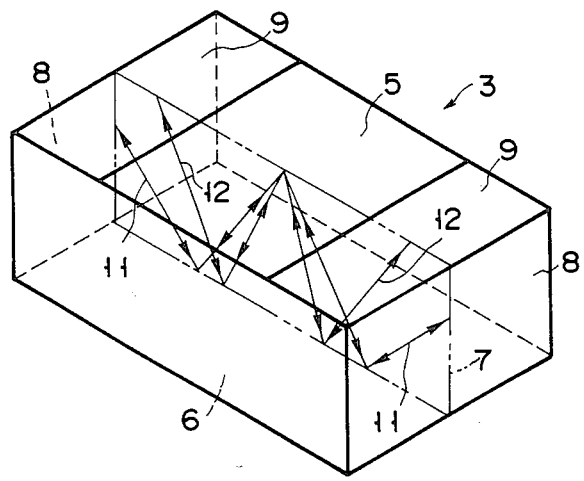
FIG. 2 is a schematic perspective view showing a reservoir section of the attachment shown in FIG. 1.
Figure 3:
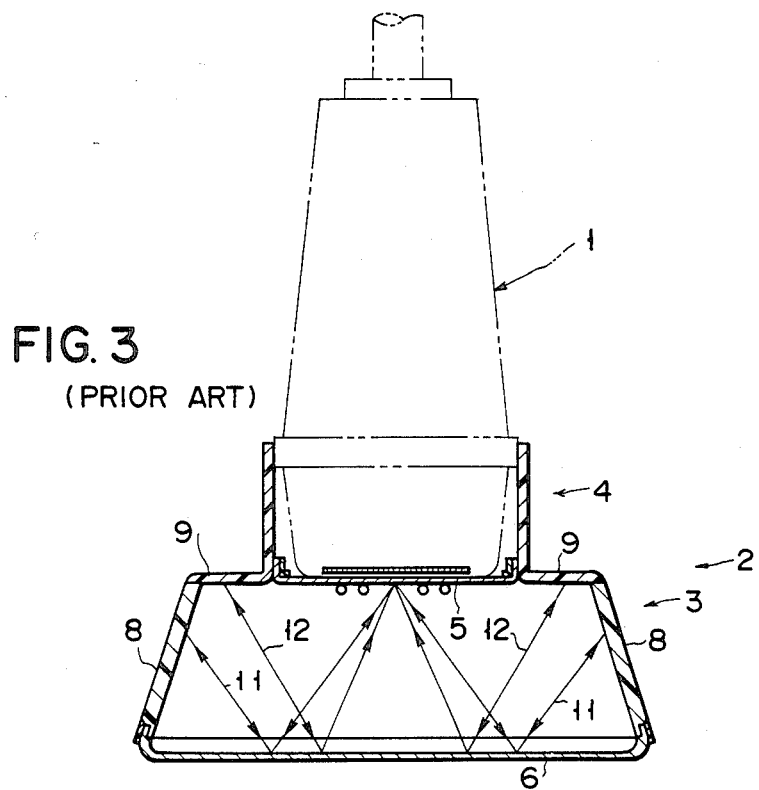
FIG. 3 is a sectional view showing a attachment for a diagnostic ultrasound probe, which is different from the attachment shown in FIG. 1.
Figure 4:
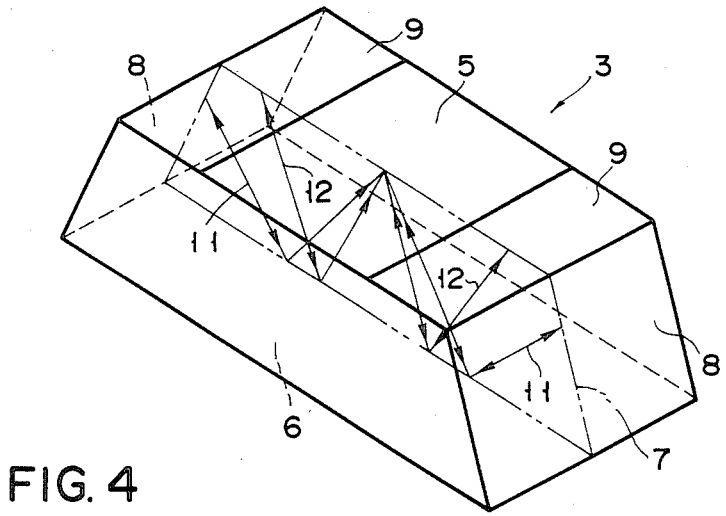
FIG. 4 is a schematic perspective view showing a reservoir section in the attachment shown in FIG. 3.
Figure 5:
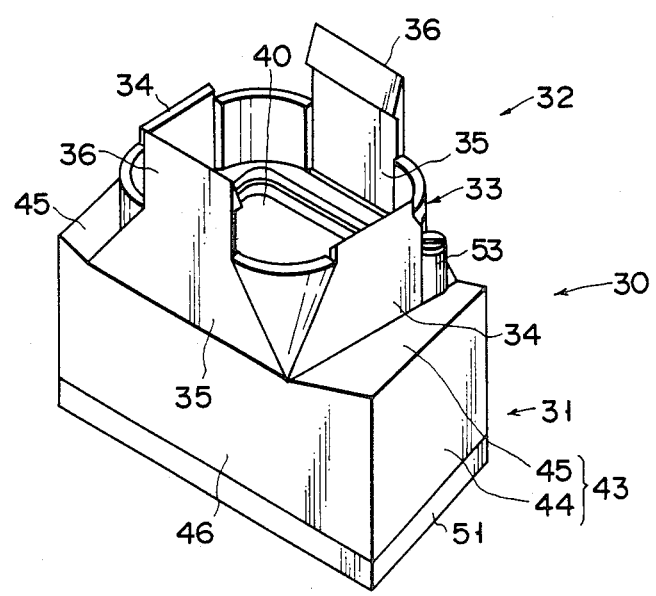
FIG. 5 is a perspective view showing an attachment for a diagnostic ultrasound probe according to the invention.

Attachment 30, as shown in FIG. 5, comprises boxlike reservoir section 31 accommodating an acoustic medium, and mounting section 32 for mounting reservoir section 31 on ultrasound probe 20.

Figure 6:
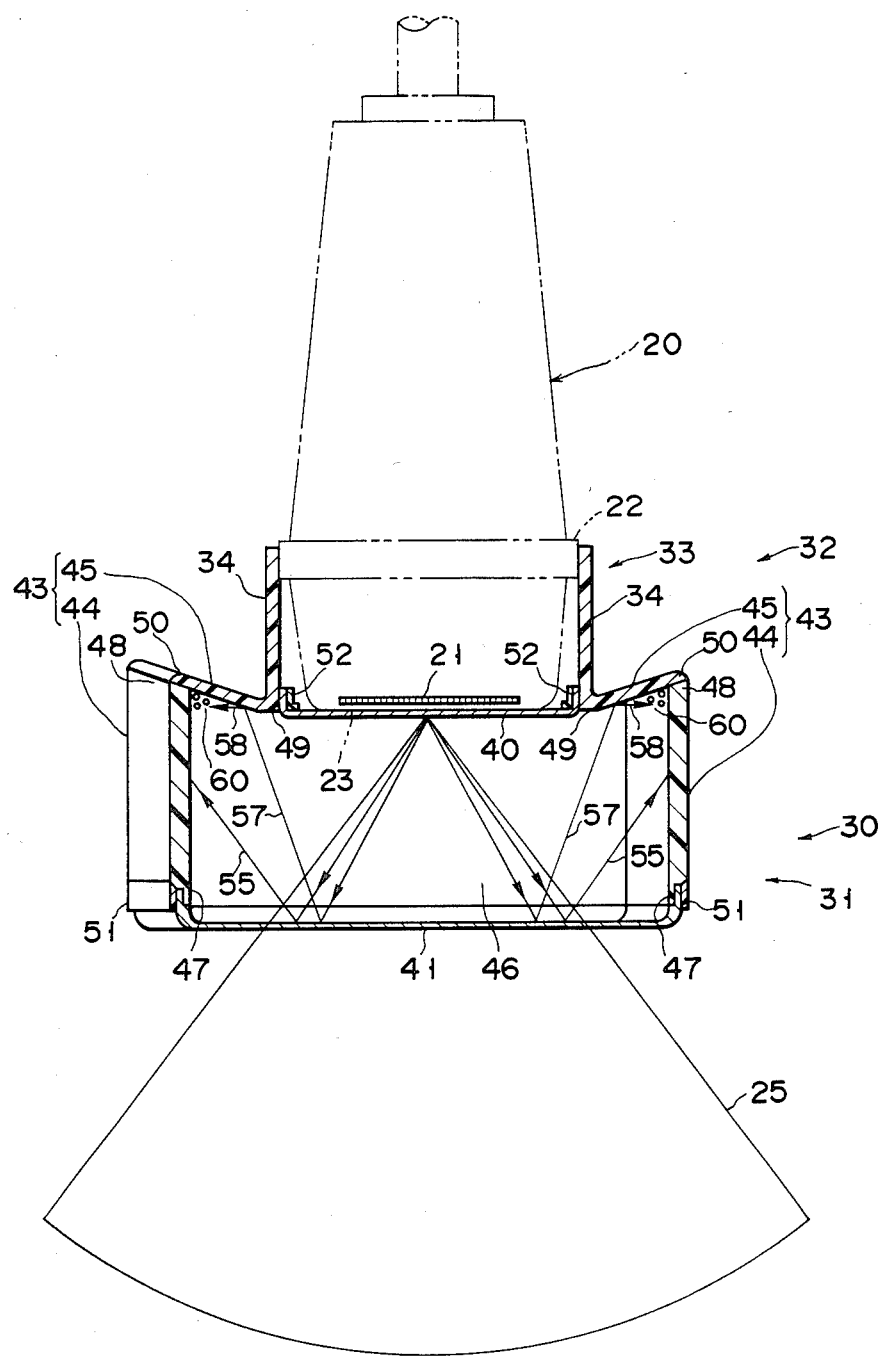
FIG. 6 is a sectional view of the attachment of FIG. 5 taken along a plane parallel to a scanning plane.
Figure 7:
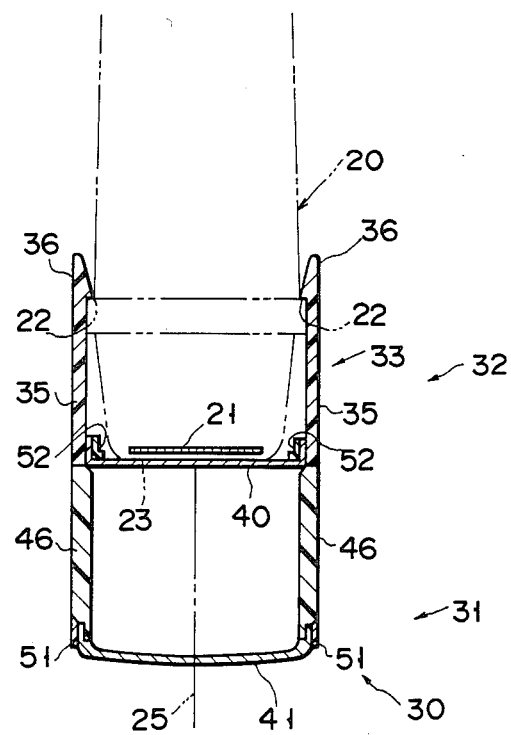
FIG. 7 is a sectional view of the attachment of FIG. 5 taken along a plane perpendicular to the scanning plane.

As shown in FIGS. 5, 6 and 7, mounting section 32 has substantially cylindrical holding section 33 having four side walls 34 and 35 for holding ultrasonic probe 20. Two side walls 35 of holding section 33 have respective hooks 36 to be engaged with shoulder 22 of ultrasound probe 20. When ultrasound probe 20 is inserted into holding section 33, hooks 36 are engaged with shoulder 22, whereby attachment 30 is mounted on ultrasound probe 20.

As shown in FIGS. 6 and 7, reservoir section 31 has auxiliary membrane 40 disposed at the upper end contact membrane 41 facing auxiliary membrane 40. Auxiliary membrane 40 and contact membrane 41 are made of silicone rubber, for instance, so that they can transmit ultrasound beam. The outer surface of auxiliary membrane 40 is in contact with beam radiating surface 23 of ultrasound probe 20. The outer surface of contact membrane 41 is in contact with the surface of the body.

Figure 9:
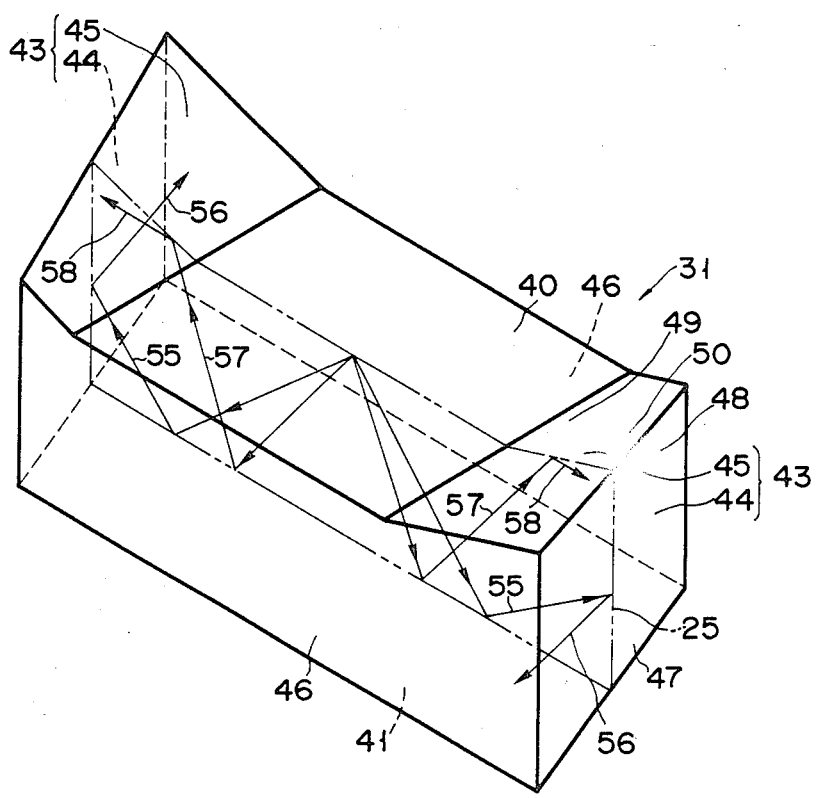
FIG. 9 is a schematic perspective view showing the reservoir section of the attachment of FIG. 5.

FIG. 9 schematically shows reservoir section 31. Reservoir section 31 will be explained schematically with reference to FIG. 9. Reservoir section 31 has a pair of first walls 43 crossing scanning plane 25 to be described later and a pair of side walls 46 facing scanning plane 25. First walls 43 connect contact membrane 41 with auxiliary membrane 40. More specifically, first wall 43 consists of a pair of side walls 44 (second walls) and a pair of top walls 45 (third walls). One end 47 (i.e., lower end) of each side wall 44 is connected to an end of contact membrane 41. One end 49 of each top wall 45 is connected to an end of auxiliary membrane 40. Other end 50 of top wall 45 is connected to other end 48 (upper end) of side wall 44. Side wall 44 is inclined with respect to scanning plane 25. Top wall 45 is inclined with respect to contact membrane 41 such that a distance between other end 50 and contact membrane 41 is greater than a distance between one end 49 and contact membrane 41. The reasons for the arrangements noted above will be described later. The upper end of each side wall 46 is connected to auxiliary membrane 40 and pair top walls 45. The lower end of each side wall 46 is connected to contact membrane 41. The inner space of reservoir section 31 is isolated from the outside by auxiliary membrane 40, contact membrane 41, pair first walls 43 (i.e., side walls 44 and top walls 45) and pair side walls 46.

Reservoir section 31 will be further described with reference to FIGS. 6 and 7, in detail. Side walls 44 and 46 are integral with one another, and constitute a cylindrical member. The edges of contact membrane 41 are secured by ring-like member 51 to one end (lower end) 47 of each side wall 44 and lower end of each side wall 46. Each top wall 45 is integral with side wall 34 of holding section 33, i.e., one end 49 of each top wall 45 is connected to the lower end of each side wall 34. The edges of auxiliary membrane 40 are secured by a ring-like member 52 to the lower end of each side wall 34 (i.e., end 49 of each top wall 45) and the lower end of each side wall 35 (FIG. 7). Further, as shown in FIG. 6, other end 50 of each top wall 45 and upper end 8 of each side wall 44 are secured to each other, and, as shown in FIG. 7, the lower end of each side wall 35 of holding section 33 and the upper end of each side wall 46 are secured to each other.

As shown in FIG. 5, holding section 33 has two inlet ports 53 (only one inlet port being shown) for pouring an acoustic medium.

Figure 14:
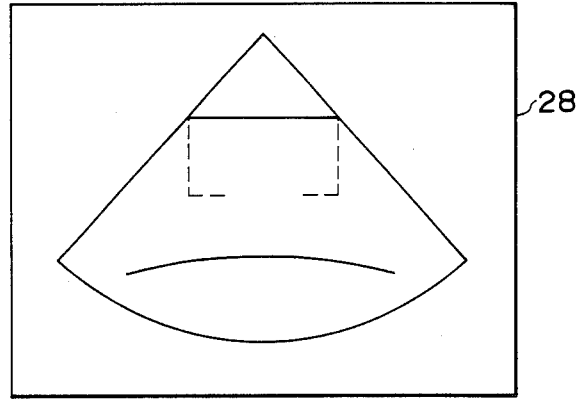
FIG. 14 is a view showing a cathode-ray tube on which a tomographic image is shown.

Ultrasound probe 20, as shown in FIG. 6, has a plurality of transducer elements 21 aligned in one direction and beam radiating surface 23. Ultrasound beam emitted from transducer elements 21 is transmitted through beam radiating surface 23, auxiliary membrane 40, acoustic medium and contact membrane 41, to be transferred to the body. In a sector system of this embodiment, as shown in FIG. 6, the ultrasound beam is deflected along scanning plane 25 in a predetermined angular range. In other words, a diseased part of the body is scanned by the ultrasound beam along scanning plane 25. The ultrasound beam reflected by the inside of the body is transmitted through contact membrane 41, ultrasound medium, auxiliary membrane 40 and beam radiating surface 23, to be received by transducer elements 21. The received ultrasound beam is converted into an electric signal, whereby the scanned diseased part of the body is drawn in a predetermined angular range on cathode-ray tube 28, as shown in FIG. 14.

According to the invention, the multiplex reflection of the ultrasound beam by first walls 43 is improved. More particularly, the multiplex reflection of the ultrasound beam by side walls 44 or top walls 45 is improved. This will be described later in detail.

Figure 8:
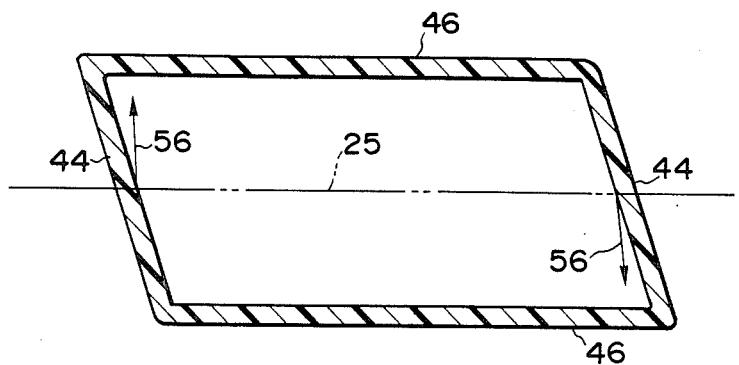
FIG. 8 is a horizontal sectional view of a reservoir section of the attachment shown in FIG. 5.

As noted before, side walls 44 are inclined with respect to scanning plane 25. This state is best shown in FIG. 8. Thus, the ultrasound beam is transferred in reservoir section 31 as follows.

When the ultrasound beam emitted from ultrasound probe 20 is transferred to contact membrane 41, it is split into a major part which is transmitted through contact membrane 41 to be transferred to the body and the remaining part which is reflected by the inner surface of contact membrane 41. The remaining part of the ultrasound beam, as shown in FIGS. 6 and 9, is transferred along first path 55 in scanning plane 25 to side walls 44. Side walls 44 are inclined with respect to scanning plane 25. Therefore, a major part of the ultrasound beam reflected by the inner surface of side walls 44 is transferred to any other than scanning plane 25, as shown by arrow 56 in FIGS. 8 and 9. Transducer elements 21 receive only the ultrasound beam along scanning plane 25. For this reason, the ultrasound beam which has been reflected by the inner surface of side walls 44 and transferred to any other than scanning plane 25 is hardly received by transducer elements 21. In other words, the component of the ultrasound beam which is reflected by the inner surface of side walls 44 and returned along first path 55 to contact membrane 41 and thence to transducer elements 21 is extremely reduced. Therefore, ultrasound beam having data of side walls 44 is hardly received by transducer elements 21, so that there is hardly a possibility that an image of side walls 44 are shown on the cathode-ray tube. That is, the appearance of artifact is reduced, so that diagnosis is never prevented by an image of side walls.

In this embodiment, the outer surface of side walls 44 need not be inclined with respect to scanning plane 25, but it is only necessary that the inner surface of side walls 44 are inclined with respect to scanning plane 25. This is so because the ultrasound beam is reflected by the inner surface of side walls 44. Further, in this embodiment both of pair side walls 44 are inclined with respect to scanning plane 25, but it is only necessary that at least one of side walls 44 is inclined with respect to scanning plane 25. In this case, an image of side wall 44 which is not inclined, is shown on cathode-ray tube 28.

According to the invention, entire side walls 44 need not be inclined with respect to scanning plane 25, but it is only necessary that portions of side walls that cross scanning plane 25 are inclined with respect to scanning plane 25. Further, it is liable that ultrasound beam reflected by the inner surface of side walls 44 and transferred to any other than scanning plane 25 is reflected by side walls 46, for instance, to be received by ultrasound probe 20. In this case, however, the ultrasound beam has been reflected a plurality of times so that the energy of the ultrasound beam has been attenuated, thus hardly giving rise to the formation of an artifact.

Further, as described above, top walls 45 are inclined with respect to contact membrane 41 such that the distance between other end 50 and contact membrane 41 is greater than the distance between one end 49 and contact membrane 41. That is, other end 50 is disposed above end 49. For this reason, the ultrasound beam is transferred in reservoir section 31 as follows.

The part of the ultrasound beam reflected by the inner surface of contact membrane 41, as shown in FIGS. 6 and 9, is transferred along second path 57 to top walls 45, which are formed in the manner as described before. Therefore, a major part of the ultrasound beam reflected by the inner surface of top walls 45 is transferred sidewise in scanning plane 25, as shown by arrows 58 in FIGS. 6 and 9. Ultrasound beam that is transferred sidewise in this way, proceeds away from transducer elements 21 and are thus hardly received by it. Therefore, the component of ultrasound beam that is reflected by the inner surface of top walls 45 and returned along second path 57 to contact membrane 41 and then to transducer elements 21 is extremely reduced. Since the ultrasound beam having data of top walls 45 is hardly received by transducer elements 21, there is hardly a possibility that an image of top walls 45 is shown on the cathode-ray tube. For this reason, there is hardly a possibility that diagnosis is prevented by an image of top walls 45.

Further, again in this case the outer surface of top walls 45 need not be inclined with respect contact member 41, and only it is necessary that the inner surface of top walls 45 be inclined with respect to contact membrane 41. Further, the pair of top walls need not be inclined with respect to, but only one of them need be inclined.

Further, as noted before, top walls 45 are inclined with respect to contact membrane 41 such that the distance between other end 50 and contact membrane 41 is greater than the distance between one end 49 and contact membrane 41. For this reason, as shown in FIGS. 6 and 9, two air storage spaces 60 are defined on both sides of auxiliary membrane 40 by top walls 45 and upper ends 48 of side walls 44. The action of air storage spaces 60 will now be described.

There is a possibility that the body is scanned with ultrasound probe 20 while the probe is disposed perpendicular to the body. In such a case, if there is air in reservoir section 31, the air, i.e., air bubbles, is displaced upwardly by buoyancy. In the prior art, such air bubbles are liable to be retained on the lower surface of auxiliary membrane 41. According to the invention, air storage spaces 60 are disposed adjacent to and above auxiliary membrane 40. For this reason, air bubbles are collected in air storage spaces 60, and unlike the prior art there is no possibility that air bubbles are retained on the inner surface of auxiliary membrane 40. Thus, ultrasound beam is never blocked by air bubbles, and there is no possibility of deterioration of the quality of tomographic image by air bubbles. That is, influence of air bubbles on ultrasound beam is extremely reduced. For this reason, unlike the prior art it is unnecessary to expel air from reservoir section 31 by replenishing with an acoustic medium. Further, other end 50 of each top wall 45 remote from auxiliary membrane 40 is located above end 49 close to auxiliary membrane 40. Therefore, air bubbles are collected in locality extremely remote from auxiliary membrane 40.

Figure 10:
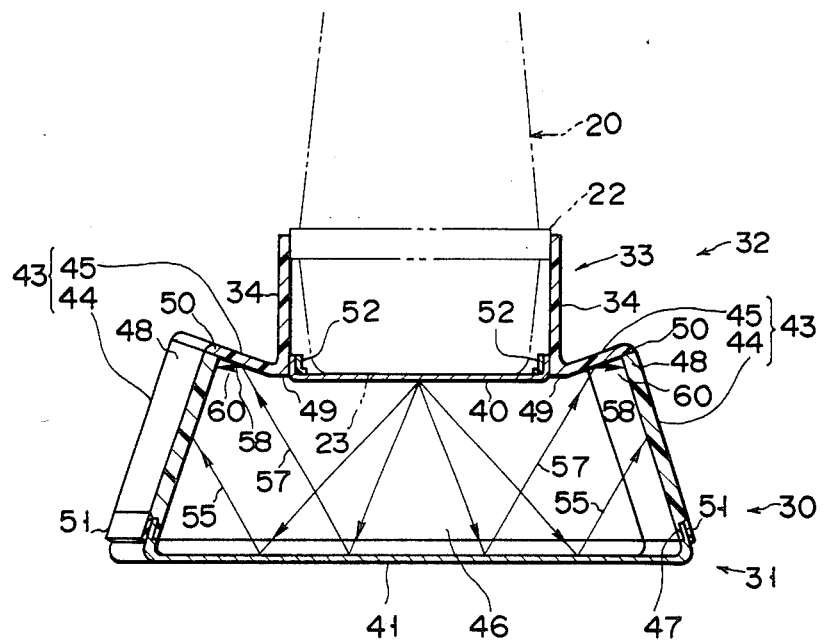
Figure 11:
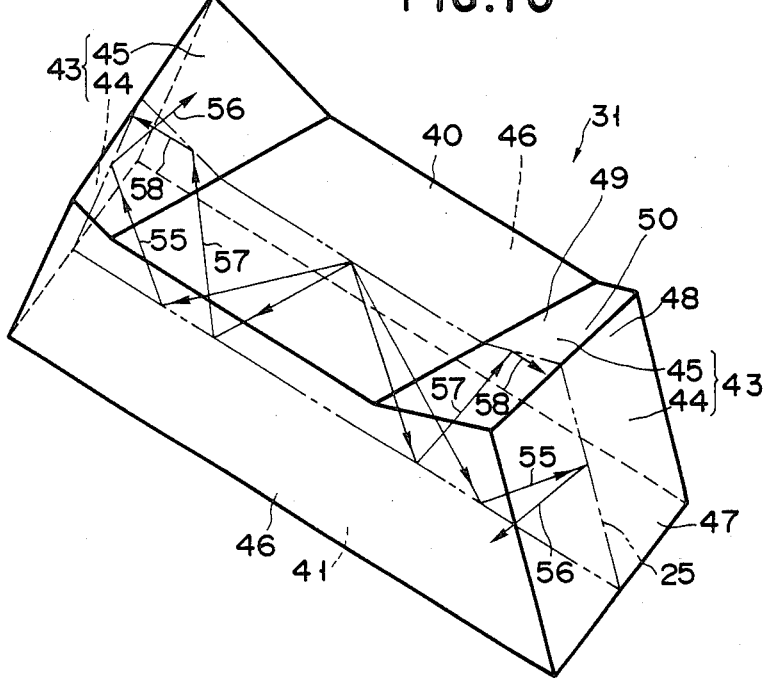

Now, a first modification of the embodiment will be described with reference to FIGS. 10 and 11.

In this modification of attachment 30, a distance between lower ends 47 of two side walls 44 is greater than a distance between upper ends 48 thereof. Like the previous embodiment, side walls 44 are inclined with respect to scanning line 25. Therefore, ultrasound beam which is reflected by the inner surface of side walls 44 and returned along first path 55 to contact membrane 41 and thence to transducer elements 21 is extremely reduced. Thus, even in this modification, there i hardly a possibility that an image of side walls is shown on cathode-ray tube 28.

Figure 12:
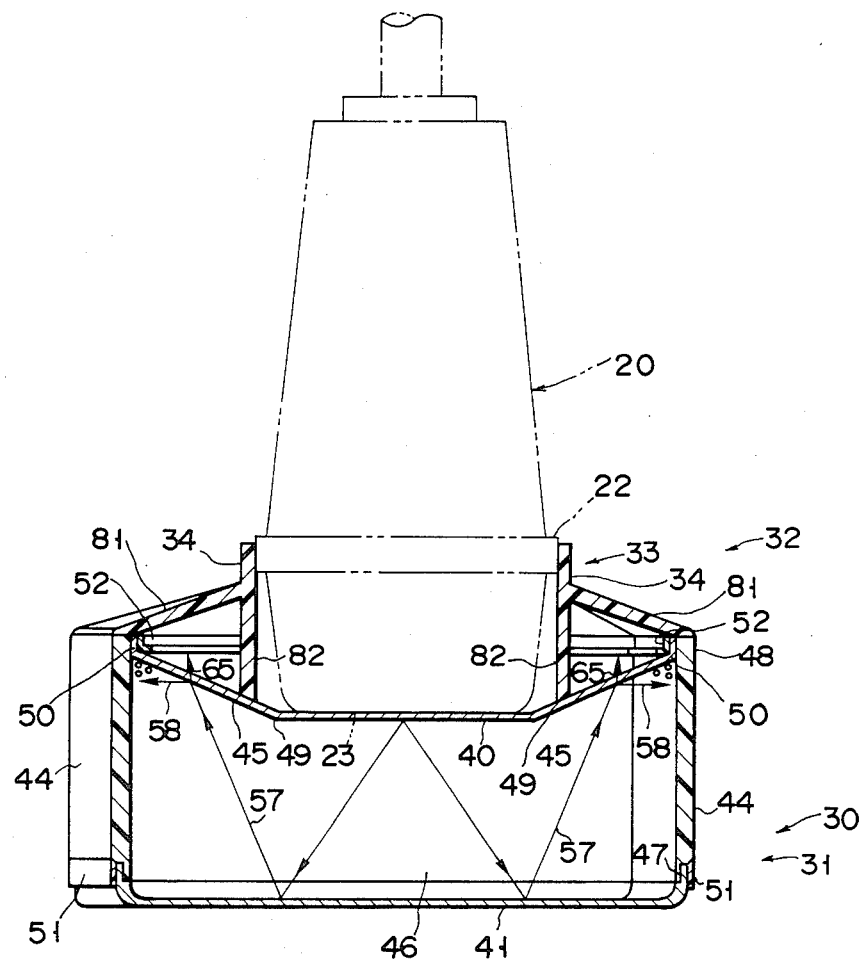
FIG. 12 is a sectional view showing a second modification of the embodiment and taken along a plane parallel to the scanning plane.

A second modification of the embodiment will now be described with reference to FIG. 12.

In this modification, top walls 45 are integral with auxiliary membrane 40, one end of each top wall 49 being connected to an end of auxiliary membrane 40. Top walls 45 are made of silicone rubber which ca transmit ultrasound beam. Other end 50 of each top wall 45 is secured by ring-like member 52 to upper end 48 of each side wall 48. Holding section 33 of mounting section 32 has wall 81, which extends obliquely downwardly from side wall 34 and has an end secured to the upper end 48 of each side wall 44, and wall 82, which extends downwardly and has a lower end in contact with each top wall 45. In this modification, therefore, when ultrasound beam reflected by contact membrane 41 is transferred to top walls 45, it is split into a component (shown by arrow 65) which is transmitted through each top wall 45 to be transferred to the outside, and the remaining component (shown by arrow 58) which is reflected by the inner surface of top walls 45 to be transferred sidewise. For this reason, in this modification ultrasound beam returned to the ultrasound probe is reduced compared to those in the previous embodiment. The possibility that an image of top walls 45 is shown on cathode-ray tube 28 thus is reduced compared to the previous embodiment.

Figure 13:
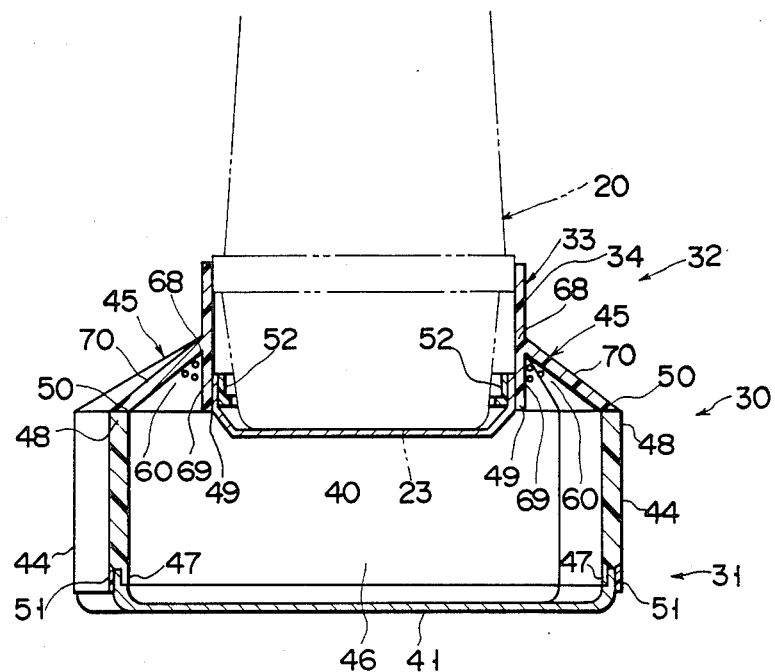
FIG. 13 is a sectional view showing a third modification of the embodiment and taken along a plane parallel to the scanning plane.

A third modification will be described with reference to FIG. 13.

In the third embodiment, each top wall 45 has vertical wall 69 (fourth wall) between end 49 and intermediate point 68 and inclined wall 70 (fifth wall) between intermediate point 68 and other end 50. Inclined walls 70 are inclined with respect to auxiliary membrane 40 such that a distance between intermediate point 68 and contact membrane 41 is greater than a distance between one end 49 and contact membrane 41, and a distance between other end 50 and it. The edges of auxiliary membrane 40 are secured by ring-like member 52 to vertical walls 69. Air storage spaces 60 are thus defined by vertical walls 69 and inclined walls 70. Like the previous embodiment, air storage spaces 60 collect air in reservoir section 31. The locality where air bubbles are collected utmost in reservoir 31, i.e., locality in the neighborhood of intermediate point 68, is comparatively close to auxiliary membrane 40. For this reason, air bubbles stored in auxiliary membrane 40 are instantly displaced to the neighborhood of intermediate point 68, that is, air bubbles are quickly collected in air storage spaces 60.

What is claimed is:

1. An attachment to an ultrasound probe having transducer means for radiating an organic body with an ultrasound beam in a scanning plane, comprising:

a housing means, having first and second transmission sections and at least one side wall, for containing an acoustic medium which transmits the ultrasound beam;

wherein said first transmission section faces the transducer means when said attachment is connected to said probe and is permeable to the ultrasound beam;

wherein said second transmission section faces the first transmission section and is permeable to the ultrasound beam, said second transmission section being adapted for contact with the organic body; and wherein said at least one side wall extends between the first and second transmission sections; said side wall including a planar surface portion adapted for contact with the acoustic medium contained in the housing means, and said planar surface portion lying in a plane which obliquely intersects the scanning plane for transferring to any other than the scanning plane, a major part of the ultrasound beam reflected by the second transmission section, transferred to the surface portion in the scanning plane and reflected by the surface portion, and for substantially preventing an ultrasound beam component reflected by the surface portion from being reflected by the second transmission section and from returning to the transducer means.

2. An attachment according to claim 1, wherein said at least one side wall includes a pair of first surface portions facing each other.

3. An attachment according to claim 2, wherein said pair of first surface portions are parallel to each other.

4. An attachment according to claim 2, wherein said pair of first surface portions are perpendicular to the second transmission section.

5. An attachment according to claim 2, wherein said pair of first surface portions are oblique to the second transmission section.

6. An attachment according to claim 2, wherein said at least one side wall includes a pair of second surface portions which connect the first surface portion together, face each other at opposite sides of the scanning plane, and are adapted to contact the acoustic medium contained in the housing.

7. An attachment according to claim 1, wherein said second transmission section is formed of a membrane, which is flexible and permits an ultrasound beam to pass therethrough, said membrane having an outer surface adapted to contact the organic body and an inner surface which is adapted to contact the acoustic medium contained in the housing.

8. An attachment according to claim 1, further comprising a fitting member connected to said housing means having a hole into which the probe is fitted; and an engaging clip connected to said fitting member for engaging an engagement step of the probe when the probe is inserted into the hole.

* * * * *